United States Patent
Kishida et al.

(10) Patent No.: US 6,790,452 B2
(45) Date of Patent: Sep. 14, 2004

(54) PIGMENT DISPERSIONS AND COSMETIC PRODUCTS CONTAINING THE SAME

(75) Inventors: Shigeru Kishida, Storrs, CT (US); Mark LePage, Webster, MA (US); Tetsuo Murata, Dallas, TX (US); William Kalriess, Tolland, CT (US); Masaru Kobayashi, Woodstock, CT (US); Isao Imai, Saitama (JP)

(73) Assignees: Miyoshi Kasei, Inc., Saitama (JP); U.S. Cosmetics Corporation, Dayville, CT (US)

( * ) Notice: Subject to any disclaimer, the term of this patent is extended or adjusted under 35 U.S.C. 154(b) by 58 days.

(21) Appl. No.: 10/178,890

(22) Filed: Jun. 25, 2002

(65) Prior Publication Data

US 2003/0235544 A1 Dec. 25, 2003

(51) Int. Cl.$^7$ .................. A61K 7/00; A61K 7/021; A61K 7/035
(52) U.S. Cl. ............... 424/401; 424/63; 424/69
(58) Field of Search ................ 424/401, 63, 69, 424/400, 64; 474/66

(56) References Cited

U.S. PATENT DOCUMENTS 4,606,914 A * 8/1986 Miyoshi .................. 424/63

FOREIGN PATENT DOCUMENTS

| JP | 58-72512 | 4/1983 |
| JP | 2000-7942 | 1/2000 |

* cited by examiner

*Primary Examiner*—Thurman K. Page
*Assistant Examiner*—Sharon Howard
(74) *Attorney, Agent, or Firm*—Westerman, Hattori, Daniels & Adrian, LLP

(57) ABSTRACT

A pigment containing particles surface treated with N-acylglycine hydroxyaluminum and/or N-acyl-N-methylglycine hydroxyaluminum, and a pigment dispersion which contains such surface treated particles and a cosmetically acceptable oily material, having excellent dispersion stability and versatility (ease of dispersion and wide range of usage), because the particles are easily and uniformly dispersed in a short period of time at a high concentration in such a cosmetically acceptable oily material, thus a cosmetic product is thereby stable as an emulsion and has better usage than existing products.

17 Claims, No Drawings

PIGMENT DISPERSIONS AND COSMETIC PRODUCTS CONTAINING THE SAME

BACKGROUND OF THE INVENTION

1. Field of Invention

The present invention relates to a pigment surface treated with a particular N-acylamino acid derivative, especially with N-acylglycine hydroxyaluminum and/or N-acyl-N-methylglycine hydroxyaluminum, a highly concentrated solid pigment dispersion (high solid pigment dispersion) containing said surface treated pigment and a cosmetically acceptable oily material, and a cosmetic product (cosmetic composition) containing said pigment dispersion, and the like.

More specifically, the present invention provides a uniform highly concentrated solid pigment dispersion in a cosmetically acceptable oily material. Moreover, a cosmetic product made through the use of said pigment dispersion presents superior emulsion stability and exhibits moist (dewy) touch important for smooth feeling, superior adhesion to the skin, and long-lasting.

2. Related Art

When pigments, especially inorganic pigments, are used as colorants in cosmetic products, a uniform dispersion with a consistent color development and a good dispersion stability are required. However, pigments, especially inorganic pigments, such as titanium oxides (dioxides or the like) and iron oxides and the like, tend to aggregate due to their fine particle size and strong hydrophilic nature. Therefore, when the pigments are dispersed in the oily materials, the poor affinity of the pigments and oily materials leads to a high viscosity of the dispersions (mixtures of said pigments and said oily materials) and it is impossible to achieve a good dispersion even with an extended shear.

On the other hand, there have been many suggestions to make pigments lipophilic (oleophilic) (refer to Japanese Patent Kokai Publication JP-A-58-72512; U.S. Pat. No. 4,606,914, and Japanese Patent Kokai Publication JP-A-2000-7942.) so far. However, even though lipophilicity (oleophilicity) of the pigments is significantly improved according to the suggestions, easy dispersible pigments which can be well dispersed by brief low-shear in the oily materials are not disclosed in these suggestions.

For example, it has been reported that N-acylamino acid salt has a good affinity with pigments and oils (oily materials), and will improve dispersibility (dispersion capability) of the pigments in the oily materials significantly. Further, when makeup products contains pigments surface treated with such N-acylamino acid salt, pigment dispersibility of the makeup products is significantly improved (refer to Japanese Patent Kokai Publication JP-A-58-72512.). The pigments treated with the N-acylamino acid salt as reported have improved affinity with the oily materials; however, the improvement thereof is insufficient, especially dispersion of the pigments in oil phase in emulsion system of water-in-oil and oil-in-water is not satisfactory. Therefore, apparent micelle size becomes inconstant, and water-droplet, in case of the water-in-oil emulsion, and oil-droplet, in case of the oil-in-water emulsion, become irregular, resulting in unstable emulsion. On the other hand, pigments that can be well dispersed by brief low-shear in the oily materials are not disclosed in any reports.

Under these above circumstances, it is desirable to develop a pigment dispersion with an excellent dispersibility as compared with prior art; that is a pigment dispersion wherein the pigment particles (particles of the pigment) can be dispersed uniformly in the cosmetically acceptable oily material in brief time (at a shorter time), and also a stable, uniform high solid dispersion of pigments (pigment particles) in the cosmetically acceptable oily material wherein the pigment particles can be uniformly dispersed in oil phase of emulsion in brief time; and a cosmetic product (cosmetic composition) with an excellent emulsion stability containing such pigment dispersion.

DISCLOSURE OF THE INVENTION

Problem to be Solved by Invention

It is an object of the present invention or a problem to be solved by the invention to provide a pigment dispersion for use in cosmetics (cosmetic products) with an improved dispersion stability and versatility (ease of dispersion and wide rage of usage) compared to the existing technology, and a cosmetic product (cosmetic composition) with an excellent emulsion stability and improved usage and feel (smooth feeling) compared to the existing cosmetic products.

SUMMARY OF THE INVENTION

The present inventors have discovered, during a study to solve the previous problem, that pigments (pigment particles) surface treated with N-acylglycine hydroxyaluminum and/or N-acyl-N-methylglycine hydroxyaluminum are easily and uniformly dispersed in short period of time in cosmetically acceptable oily material, and that the pigment dispersion containing these pigments (pigment particles) and the cosmetically acceptable oily material will provide with an excellent dispersion stability and versatility (ease of dispersion and wide rage of usage) because of the ability of these pigments (pigment particles) to be uniformly dispersed at a high concentration in the cosmetically acceptable oily material. Further, it has been also discovered that a cosmetic product (cosmetic composition) which contains these surface treated pigments (pigment particles) or the pigment dispersion containing these surface treated pigments, has uniform and stable micelles, especially in water-in-oil and oil-in-water emulsions, and is stable as an emulsion and has a better usage than the existing products because the pigments (pigment particles) are not only very lipophilic (good affinity with the oily materials) and very but also uniformly dispersed in the oily materials. The above variety of knowledge has led to the completion of the present invention.

That is, the present invention lies in a surface treated pigment (referred to as the surface treated pigment of the present invention) for a cosmetic product, wherein the surface of the pigment particles is coated with N-acylglycine hydroxyaluminum and/or N-acyl-N-methylglycine hydroxyaluminum (referred to as the surface treatment agent (s) used in the present invention). In other words, the present invention lies in a surface treated pigment for a cosmetic product comprising particles (pigment particles) the surface of which is coated with N-acylglycine hydroxyaluminum and/or N-acyl-N-methylglycine hydroxyaluminum.

Furthermore, the N-acyl groups of said N-acylglycine hydroxyaluminum and said N-acyl-N-methylglycine hydroxyaluminum are independent from each other, and each may be selected from a N-myristoyl group, a N-lauroyl group, a N-palmitoyl group, and a N-stearoyl group, preferably a N-myristoyl group to provide a surface treated pigment with a better dispersibility. According to the present invention, a pigment to be treated (pigment before surface treatment, pigment used for production of the surface treated pigment), if selected from titanium oxides and iron oxides, such as $TiO_2$, $FeO \cdot OH$, $Fe_2O_3$ and $Fe_3O_4$, may be rendered with superior dispersibility by surface treatment.

The present invention also lies in, as an another form, a pigment dispersion comprising the surface treated pigment described above, the surface of which (the surface of the pigment particles) is coated with the N-acylglycine hydroxyaluminum and/or the N-acyl-N-methylglycine hydroxyaluminum, and a cosmetically acceptable oily material.

The pigment dispersion of the present invention, when the said cosmetically acceptable oily material (oil solution) is selected from silicone fluids (oils) and fatty acid esters (fatty acid ester oils or the like), delivers an excellent dispersion due to ease of dispersing pigments (pigment particles). Moreover, the pigment dispersion of the present invention has an excellent fluidity (liquidity) because surface treated pigments (pigment particles) are uniformly and stably dispersed in the cosmetically acceptable oily material. Pigment dispersions with viscosity preferably equal to or less than 100,000 mPa.sec (at highest 100,000 mPa.sec, not more than 100,000 mPa.sec), more preferably from about (approxymately) 100,000 to about 500 mPa.sec, most preferably from about 5,000 to about 1,000 mPa.sec may be provided according to the present invention.

The present invention lies in, as an another form, a cosmetic product (referred to as a cosmetic product of the present invention) comprising said surface treated pigment(s) or said pigment dispersion(s).

Besides, it is especially preferable to use the cosmetic product of the present invention as a liquid foundation, a lip gloss, an eyeliner, a mascara, a cream eye-shadow, a tinted moisturizer, or a sunscreen product.

PREFERRED EMBODIMENTS OF THE INVENTION

The present invention is described in detail below for embodiments of the invention.

The present invention includes a pigment surface treated with a particular N-acylamino acid derivative, especially N-acylglycine hydroxyaluminum and/or N-acyl-N-methylglycine hydroxyaluminum, a pigment dispersion comprising said surface treated pigment and a cosmetically acceptable oily material, and a cosmetic product comprising said pigment dispersion, and the like. Besides, the methods of preparing the pigment dispersions and the cosmetic products using the surface treated pigments of the present invention are further illustrated below; however, are not intended to limit the scope of the present invention.
(Surface Treated Pigments of the Present Invention)

The surface treated pigments of the present invention include pigments surface treated with the N-acylglycine hydroxyaluminum and/or the N-acyl-N-methylglycine hydroxyaluminum, and are used, as an example, in admixture with the cosmetically acceptable oily materials as a pigment dispersion or the like for a cosmetic product.

The N-acylglycine hydroxyaluminum used in the present invention typically has a composition in which one or two molecules of N-acylglycine are bonded to an aluminum atom via a carboxyl group, and the aluminum atom carries at least one hydroxyl group. Empirically, the ratio of N-acylglycine to aluminum is most preferably 2 to 1. A composition in which N-acylglycine is from 1.5 to 2.5 relative to an aluminum atom (1) is acceptable.

Besides, as described above, according to the present invention, the N-acylglycine hydroxyaluminum may be selected, as a single or a mixture, from N-acylglycine hydroxyaluminum with the ratio of N-acylglycine to aluminum (2:1) and that with other ratios. Further, for the N-acylglycine hydroxyaluminum with the ratio of N-acylglycine to aluminum (2:1), N-acylglycine hydroxyaluminum carrying two identical N-acyl groups (e.g. two N-myristoyl groups), or that carrying two different N-acyl groups (e.g. one N-myristoyl group and another N-stearoyl group) may be used individually (as a single) or as a mixture.

The N-acyl-N-methylglycine hydroxyaluminum used in the present invention typically has a composition in which one or two molecules of N-acyl-N-methylglycine are bonded to an aluminum atom via a carboxyl group, and the aluminum atom carries at least one hydroxyl group. Empirically, the ratio of N-acyl-N-methylglycine to aluminum is most preferably 2 to 1. A composition in which N-acyl-N-methylglycine is from 1.5 to 2.5 relative to an aluminum atom (1) is acceptable.

Besides, as described above, according to the present invention, the N-acyl-N-methylglycine hydroxyaluminum may be selected, as a single or a mixture, from N-acyl-N-methylglycine hydroxyaluminum with the ratio of N-acyl-N-methylglycine to aluminum (2:1) and that with other ratios. For the N-acyl-N-methylglycine hydroxyaluminum with the ratio of N-acyl-N-methylglycine to aluminum (2:1), N-acyl-N-methylglycine hydroxyaluminum carrying two identical N-acyl groups (e.g. two N-myristoyl groups), or that carrying two different N-acyl groups (e.g. one N-myristoyl group and another N-stearoyl group) may be used individually (as a single) or as a mixture.

The present invention includes pigments (pigment particles) surfaces of which are concurrently treated with the N-acylglycine hydroxyaluminum and the N-acyl-N-methylglycine hydroxyaluminum. The mixture of two or more pigments which are surface treated with each surface treatment agent is also included in the present invention.

There is no particular limitation to the N-acylglycine hydroxyaluminum and the N-acyl-N-methylglycine hydroxyaluminum used in the present invention. They may be purchased from a market. The acyl groups of said N-acylglycine hydroxyaluminum and said N-acyl-N-methylglycine hydroxyaluminum are indepently selected, each preferably from those with 12 to 18 carbon atoms; more preferably from a single or a mixture of a myristoyl group, a lauroyl group, a palmitoyl group, and a stearoyl group, and most preferably from a myristoyl group.

There is no particular limitation to the pigments to be surface treated according to the present invention insofar as it is cosmetically acceptable. The pigments can be preferably selected from oxides of aluminum, calcium, magnesium, cerium, silicon, zirconium, titanium, zinc and iron, and ultramarines, more preferably selected from titanium oxides and iron oxides, such as $TiO_2$, $FeO \cdot OH$, $Fe_2(OH)_6$, $Fe_2O_3$ and $Fe_3O_4$.

For the said pigments to be surface treated, extender pigments, such as talc, kaolin, micas, such as white mica powder, sericite and the like, magnesium carbonate, aluminum silicate, magnesium silicate, calcium silicate, clays and the like, may be used with the said oxides to improve versatility. The amount of the extender pigments used may be determined based on the specific needs; however, is preferably from 0 to about (approximately) 50%, by weight, more preferably from 0 to about 20%, by weight of (based on) the total (entire) amount of the said pigment ingredient(s) including such extender pigment ingredient(s).

The amount of the surface treatment agent(s), the N-acylglycine hydroxyaluminum and the N-acyl-N-methylglycine hydroxyaluminum, used in the present invention to coat the pigments is preferably from about (approximately) 0.2% to about 20%, by weight, more preferably from about 2% to about 15%, by weight, based on the pigments before the surface treatment (pigments to be surface treated), depending on the type and specific surface area of the pigments (particles) to be surface treated.

According to the present invention, pigments (particles) to be surface treated can be surface treated with said surface treatment agent(s) by any known methods for surface treatment (coating). For example, pigments (particles) to be surface treated are dispersed in water to form from about (approximately) 5 to about 30% by weight suspension, and water-soluble salt of N-acyl-N-methylglycine is added thereto in an amount of from 0.2 to 20% by weight with respect to the pigments and stirring is carried out until uniform. While this suspension (mixture) is being stirred, from 1 to 30% aqueous solution of the water-soluble aluminum salt is gradually added thereto dropwise in such an amount that the water-soluble aluminum salt is from 0.65 to 2 molar equivalents with respect to the N-acyl-N-methylglycine water-soluble salt. If necessary, its pH is adjusted to 4.0. Thereby, the N-acyl-N-methylglycine water-soluble salt reacts with the water-soluble aluminum salt to cause the reaction product, N-acyl-N-methylglycine hydroxyaluminum, to be successively oriented and adsorbed onto the surface(s) of the pigment particles. Stirring is continued for about (approximately) 60 minutes to allow more reaction (aging). The resultant is filtered, washed with water, and dried at from 80 to 120° C. or so to obtain a surface treated pigment.

Besides, surface treatment (coating) with N-acylglycine hydroxyaluminum can be done in a similar manner as above.

The surfaces of the surface treated pigments of the present invention may be further coated by appropriate oily materials to produce pigments with additional coatings. The oily material(s) described above may be selected from those with less affinity with water, for example oils, such as silicone oil, mineral oil (liquid paraffin), squalane, petrolatum, microcrystalline wax, polyisobutylene, myristic acid, stearic acid, lauric acid, ceresine, isopropylmyristate, dodecylmyristate, coconut oil, linseed oil, lanolin, beeswax, olive oil, stearyl alcohol, mink oil, oleyl alcohol, glycerylresinate and glycerylmonostearate and used as a single or a mixture thereof.

Besides, the coating of the surface treated pigment with said appropriate oily materials can be done without any difficulties. For example, to the aqueous mixture (suspension) of the surface treated pigment of the present invention, a dosage (an optimum), and preferably an amount of from approximately 0.5 to 10% by weight, of the appropriate oily material(s) described above based on the surface treated pigment is added as it is, or as a mixture with alcohols, petroleum solvent(s), or other appropriate organic solvent(s) for dissolution, and is stirred sufficiently. Further, the resultant is dehydrated by centrifuge and dried to obtain a desired surface treated pigment. The obtained surface treated pigments with additional uniform coating of the oily materials are more dispersible due to the synergic effect of surface treatment (coating) of the present invention and additional coating provided by the oily materials. The surface treated pigments with additional uniform coating of the oily materials, when incorporated in cosmetic products, will provide cosmetic products with more emulsion stability.

(Pigment Dispersions of the Present Invention)

The pigment dispersions of the present invention contain the surface treated pigments described above (surface treated pigments of the present invention). The said surface treated pigments can be prepared as previously described. On the other hand, the said surface treated pigments can be uniformly dispersed in the cosmetically acceptable oily materials (oil solutions; oil phases) in a short period of time to produce high solid pigment dispersion. The pigment dispersions of the present invention are excellent in dispersion stability and versatility (ease of dispersion and wide rage of usage), in cosmetic products.

There is no restriction on the oily materials used in the present invention as long as cosmetically acceptable. Examples are oils and fats, such as safflower oil, soybean oil, evening primrose oil, grape seed oil, rose hips oil, coconut oil, almond oil, sesame oil, wheat germ oil, corn oil, cottonseed oil, avocado oil, olive oil, camellia oil, persic oil, castor oil, peanut oil, hazelnut oil, macadamia oil, meadowfoam oil, cacao butter, shea butter, Japan wax, palm oil, palm kernel oil, beef tallow, horse fat, mink oil, milk fat, egg yolk oil, and turtle oil; silicone fluids (oils), such as methylpolysiloxane, methyl phenylpolysiloxane, octamethyl cyclotetrasiloxane, decamethyl cyclopentasiloxane, dodecamethyl cyclohexasiloxane, alkyl-modified silicone, and polyether-modified silicone; and fatty acid esters (fatty acid ester oils or the like), such as isopropyl isostearate, ethyl oleate, octyldodecyl oleate, octyldodecyl myristate, diisostearyl malate, glyceryl tricaprylate, isooctyl isononanoate, and glyceryl tri-2-ethylhexanate. Among them, preferably at least one of the silicone oils and the fatty acid esters, may be selected.

According to the present invention, one or more types of said surface treated pigments may be dispersed in a cosmetically acceptable oily material to provide the pigment dispersion of the present invention. Such pigment dispersion(s) is included in the present invention as a matter of course.

In the mixing/dispersing method for dispersing said surface treated pigments in said cosmetically acceptable oily materials, any suitable methods known may be employed. Examples of such methods in producing pigment dispersion are by wet mixing/dispersing equipment such as, propeller mixer, high speed mixer, disperser, homogenizer, fluid-jet-mill, colloid mill, disk grinder, bead mill, and sand mill, but not limited to these.

In the pigment dispersion of the present invention, there is no restriction on the amount of each component, the surface treated pigment(s) and the cosmetically acceptable oily material(s); however, the surface treated pigment level is preferably from about (approximately) 40% to about 70% by weight and the cosmetically acceptable oily material (oil phase) level is preferably from about (approximately) 30% to about 60% by weight, respectively, of (based on) the pigment dispersion.

The pigment dispersion of the present invention has, as previously described, an excellent fluidity. Therefore, it allows more flexibility for cosmetic formulations. Especially, the present invention provides a fluidic pigment dispersion, with viscosity of preferably equal to or less than 100,000 mPa.sec (at highest 100,000 mPa.sec, not more than 100,000 mPa.sec), more preferably from about (approximately) 100,000 to about 500 mPa.sec, most preferably from about 5,000 to about 1,000 mPa.sec, to be used in cosmetic formulations with significant flexibility. Besides, the said dispersion is unique and innovative. On the other hand, its viscosity can be measured with no difficulties; for example, it can be measured with Brookfield viscometer, type B viscometer or the like.

(Cosmetic Products of the Present Invention)

The cosmetic products of the present invention are cosmetic products which contain said surface treated pigments (surface treated pigments of the present invention) or said pigment dispersions (pigment dispersions of the present invention). The said surface treated pigments may be prepared as illustrated earlier. On the other hand, the said pigment dispersions may be prepared as illustrated earlier.

The cosmetic products of the present invention can be produced without any difficulties using existing technologies. Especially, technologies used to produce cosmetic products with surface treated pigments are useful in making emulsions and the like and obtaining the desired cosmetic products.

In the cosmetic products of the present invention, when the surface treated pigments described above (surface treated pigments of the present invention) are used to produce the cosmetic products, the amount of the surface treated pigments and the cosmetically acceptable oily materials used may be determined based on the desired properties of the cosmetic products; however, the surface treated pigment can be incorporated preferably at a usage range of from about (approximately) 1% to about 50% by weight, more preferably from about 5% to about 30% by weight, and most preferably from about 10% to about 20% by weight; and the cosmetically acceptable oily material (oil solution;

oil phase) can be incorporated preferably at a usage range of from about (approximately) 5% to about 99% by weight, more preferably from about 10% to 80% by weight, and most preferably from about 20% to about 50% by weight, of (based on) the total ingredients therein.

On the other hand, in the cosmetic products of the present invention, when the pigment dispersion described above (pigment dispersion of the present invention) is used to produce the cosmetic product, the amount of the pigment dispersion used optionally may be determined in the same manner based on the desired properties of the cosmetic products; however, the pigment dispersion can be incorporated preferably at a usage range of from about (approximately) 1.5% to about 50% by weight, more preferably from about 7.5% to about 45% by weight, and most preferably from about 15% to about 30% by weight, of (based on) the total ingredients therein.

The cosmetic products of the present invention may be formed as emulsion by adding water to the surface treated pigments or the pigment dispersions of the present invention, and the amount of water is preferably from 0 to about (approximately) 94% by weight, more preferably from about 5% to about 80% by weight, and most preferably from about 10% to about 60% by weight, of (based on) the total ingredients therein.

The cosmetic products of the present invention may be in any product forms or in any forms, such as powder, pressed powder, liquid, and stick, and the like; and in any types, such as emulsion-type, oil-type and the like. Examples of such cosmetic products are loose powder, foundation (liquid foundation or the like), pressed powder, eye-shadow (cream eye-shadow or the like), lipstick, lipgloss, eyeliner, mascara, eye-brow, skincare cream, powder lotion, tinted moisturizer, sunscreen product, and the like; however, liquid foundation, lipgloss, eyeliner, mascara, cream eye-shadow, tinted moisturizer, sunscreen product and the like are preferable.

The cosmetic products of the present invention may, in addition to said surface treated pigments (the surface treated pigments of the present invention) or said pigment dispersions (the pigment dispersions of the present invention), contain other ingredients which are used routinely in cosmetics, such as surfactants, UV absorbers, antiseptics, anti-oxidants, film formers, humectants, thickeners, dyes, fragrants and the like, in the range without impairing the object(s) of the present invention and the effect(s) obtained in the present invention.

EXAMPLES

The present invention is further described with reference to the following examples and comparative examples; however, the examples are not intended to limit the scope of the present invention.

Example 1

(Preparation of Surface Treated Pigment-1)
1. To 900 parts of pure water, 80 parts of titanium dioxide and 20 parts of talc, all by weight, were added and dispersed sufficiently (fully).
2. To 100 parts by weight of pure water at 60° C., 5 parts of sodium N-myristoyl-N-methylglycine were added and dissolved sufficiently.
3. To a mixture of titanium dioxide-talc (pigment suspension) from the resulting mixture of (1) above, an aqueous solution of surface treatment agent (finishing agent) obtained in (2) above was added and stirred sufficiently.
4. The pH value of the mixture obtained in (3) above was adjusted to 4.0 with dropwise addition of 1N aqueous solution of aluminum chloride while stirring.
5. After stirring for 60 minutes, it was filtered, washed with water, and dried at 115° C. for 12 hours. The resulting mass was pulverized to obtain aluminum N-myristoyl-N-methylglycine coated (treated) titanium dioxide/talc admixture.

Example 2

(Preparation of Surface Treated Pigment-2)
1. To 900 parts of pure water, 80 parts of yellow iron oxide and 20 parts of talc, all by weight, were added and dispersed sufficiently.
2. To 200 parts by weight of pure water at 60° C., 7 parts of sodium N-myristoyl-N-methylglycine were added and dissolved sufficiently.
3. To a mixture of yellow iron oxide-talc (pigment suspension) from the resulting mixture of (1) above, an aqueous solution of surface treatment agent (finishing agent) obtained in (2) above was added and stirred sufficiently.
4. The pH value of the mixture obtained in (3) above was adjusted to 4.0 with dropwise addition of 1N aqueous solution of aluminum chloride while stirring.
5. After stirring for 60 minutes, it was filtered, washed with water, and dried at 115° C. for 12 hours. The resulting mass was pulverized to obtain aluminum N-myristoyl-N-methylglycine coated (treated) yellow iron oxide/talc admixture.

Example 3

(Preparation of Surface Treated Pigment-3)
Aluminum N-myristoyl-N-methylglycine coated (treated) red iron oxide/talc admixture was produced in the same way as in Example 2 except using red iron oxide; "Bengara" (80 parts by weight) in place of the yellow iron oxide in Example 2.

Example 4

(Preparation of Surface Treated Pigment-4)
Aluminum N-myristoyl-N-methylglycine coated (treated) black iron oxide/talc admixture was produced in the same way as in Example 2 except using black iron oxide (80 parts by weight) in place of the yellow iron oxide in Example 2.

Example 5

(Preparation of Surface Treated Pigment-5)
1. To 900 parts by weight of pure water, 100 parts by weight of titanium dioxide were added and dispersed sufficiently.
2. To 100 parts by weight of pure water at 60° C., 7 parts by weight of sodium N-lauroylglycine were added and dissolved sufficiently.
3. To the resulting titanium dioxide dispersion (pigment suspension) obtained in (1) above, an aqueous solution of surface treatment agent (finishing agent) obtained in (2) above was added and stirred sufficiently.
4. The pH value of the mixture obtained in (3) above was adjusted to 4.0 with drop wise addition 1N aqueous solution of aluminum chloride while stirring.
5. After stirring for 60 minutes, it was filtered, washed with water, and dried at 115° C. for 12 hours. The resulting mass was pulverized to obtain aluminum N-lauroylglycine coated (treated) titanium dioxide.

Example 6

(Preparation of Surface Treated Pigment-6)
1. To 900 parts by weight of pure water, 100 parts by weight of red iron oxide were added and dispersed sufficiently.
2. To 200 parts by weight of pure water at 60° C., 7 parts by weight of sodium N-lauroylglycine were added and dissolved sufficiently.
3. To the resulting red iron oxide dispersion (pigment suspension) obtained in (1) above, an aqueous solution of surface treatment agent (finishing agent) obtained in (2) above was added and stirred sufficiently.
4. The pH value of the mixture obtained in (3) above was adjusted to 4.0 with dropwise addition of 1N aqueous solution of aluminum chloride while stirring.
5. After stirring for 60 minutes, it was filtered, washed with water, and dried at 115° C. for 12 hours. The resulting mass was pulverized to obtain aluminum N-lauroylglycine coated (treated) red iron oxide.

Example 7
(Preparation of Pigment Dispersion-1)
To 65 parts by weight of the aluminum N-myristoyl-N-methylglycine coated (treated) titanium dioxide/talc admixture obtained in Example 1, 35 parts by weight of cyclomethicone (DC 345 Fluid, Dow Corning) was added and mixed for 5 minutes at 4,000 rpm by homogenizer (Tokushu Kika Kogyo Co., Ltd.) for dispersion. The obtained paste (pigment dispersion) was fluidic and its viscosity was 72,000 mPa.sec (measured with Brookfield viscometer, Shibaura System).

Example 8
(Preparation of Pigment Dispersion-2)
Fluidic paste was obtained in the same way as in Example 7 except using the aluminum N-myristoyl-N-methylglycine coated (treated) yellow iron oxide/talc admixture (65 parts by weight) obtained in Example 2 in place of the aluminum N-myristoyl-N-methylglycine coated (treated) titanium dioxide/talc admixture. The viscosity of the obtained paste was 85,000 mPa.sec (measured with Brookfield viscometer, Shibaura System).

Example 9
(Preparation of Pigment Dispersion-3)
Fluidic paste was obtained in the same way as in Example 7 except using the aluminum N-myristoyl-N-methylglycine coated (treated) red iron oxide/talc admixture (65 parts by weight) obtained in Example 3 in place of the aluminum N-myristoyl-N-methylglycine coated (treated) titanium dioxide/talc admixture. The viscosity of the obtained paste was 68,000 mpa.sec (measured with Brookfield viscometer, Shibaura System).

Example 10
(Preparation of Pigment Dispersion-4)
Fluidic paste was obtained in the same way as in Example 7 except using the aluminum N-myristoyl-N-methylglycine coated (treated) black iron oxide/talc admixture (65 parts by weight) obtained in Example 4 in place of the aluminum N-myristoyl-N-methylglycine coated (treated) titanium dioxide/talc admixture. The viscosity of the obtained paste was 75,000 mPa.sec (measured with Brookfield viscometer, Shibaura System).

Comparative Example 1
(Preparation of Surface Treated Pigment-7)
1. To 900 parts of pure water, 80 parts of titanium dioxide and 20 parts of talc, all by weight, were added and dispersed sufficiently.
2. To 100 parts by weight of pure water at 60° C., 3 parts by weight of sodium N-stearoyl-L-glutamate were added and dissolved sufficiently.
3. To a mixture of titanium dioxide-talc (pigment suspension) from the resulting mixture of (1) above, an aqueous solution of surface treatment agent (finishing agent) obtained in (2) above was added and stirred sufficiently.
4. The pH value of the mixture obtained in (3) above was adjusted to 4.0 with dropwise addition of 1N aqueous solution of aluminum chloride while stirring.
5. After stirring for 60 minutes, it was filtered, washed with water, and dried at 115° C. for 12 hours. The resulting mass was pulverized to obtain aluminum N-stearoyl-L-glutamate coated (treated) titanium dioxide/talc admixture.

Comparative Example 2
(Preparation of Surface Treated Pigment-8)
Aluminum N-stearoyl-L-glutamate coated (treated) yellow iron oxide/talc admixture was produced in the same way as in Comparative Example 1 except using yellow iron oxide (80 parts by weight) in place of the titanium dioxide in Comparative Example 1.

Comparative Example 3
(Preparation of Surface Treated Pigment-9)
Aluminum N-stearoyl-L-glutamate coated (treated) red iron oxide/talc admixture was produced in the same way as in Comparative Example 1 except using red iron oxide (80 parts by weight) in place of the titanium dioxide in Comparative Example 1.

Comparative Example 4
(Preparation of Surface Treated Pigment-10)
Aluminum N-stearoyl-L-glutamate coated (treated) black iron oxide/talc admixture was produced in the same way as in Comparative Example 1 except using black iron oxide (80 parts by weight) in place of the titanium dioxide in Comparative Example 1.

Comparative Example 5
(Preparation of Pigment Dispersion-5)
To 65 parts by weight of the mixture of titanium dioxide-talc obtained in the mixture of 80 parts by weight of titanium dioxide and 20 parts by weight of talc, 35 parts by weight of cyclomethicone (DC 345 Fluid, Dow Corning) was added and mixed. However, obtained paste was not fluidic (pigment dispersion); thus, viscosity thereof was unable to be measured.

Comparative Example 6
(Preparation of Pigment Dispersion-6)
To 65 parts by weight of the aluminum N-stearoyl-L-glutamate coated (treated) titanium dioxide/talc admixture obtained in Comparative Example 1, 35 parts by weight of cyclomethicone (DC 345 Fluid, Dow Corning) was added and mixed for 5 minutes at 4,000 rpm by homogenizer (Tokushu Kika Koglyo Co., Ltd.). The obtained paste was fluidic and its viscosity was 39,000 mPa·sec (measured with Brookfield viscometer, Shibaura System).

Comparative Example 7
(Preparation of Pigment Dispersion-7)
Fluidic paste was obtained in the same way as in Comparative Example 6 except using the aluminum N-stearoyl-L-glutamate coated (treated) yellow iron oxide/talc admixture obtained in Comparative Example 2 in place of the aluminum N-stearoyl-L-glutamate coated (treated) titanium dioxide/talc admixture. The viscosity of the obtained paste was 53,000 mPa.sec (measured with Brookfield viscometer, Shibaura System).

Comparative Example 8
(Preparation of Pigment Dispersion-8)
Fluidic paste was obtained in the same way as in Comparative Example 6 except using the aluminum N-stearoyl-L-glutamate coated (treated) red iron oxide/talc admixture obtained in Comparative Example 3 in place of the aluminum N-stearoyl-L-glutamate coated (treated) titanium dioxide/talc admixture. The viscosity of the obtained paste was 31,000 mPa.sec (measured with Brookfield viscometer, Shibaura System).

Comparative Example 9
(Preparation of Pigment Dispersion-9)

Fluidic paste was obtained in the same way as in Comparative Example 6 except using the aluminum N-stearoyl-L-glutamate coated (treated) black iron oxide/talc admixture obtained in Comparative Example 4 in place of the aluminum N-stearoyl-L-glutamate coated (treated) titanium dioxide/talc admixture. The viscosity of the obtained paste was 41,000 mPa.sec (measured with Brookfield viscometer, Shibaura System).

Example 11
(Evaluation of Dispersibility of Pigment Dispersion)

Dispersibility of pigment dispersion on the pastes (pigment dispersion) obtained from Examples 7 through 10 and the pastes from Comparative Examples 6 through 9 was evaluated using grind gage (Model 232, Ericsen). All the pigment dispersion pastes obtained from Examples 7 through 10 demonstrated good dispersibility. On the other hand, all the pigment dispersion pastes obtained from Comparative Examples 6 through 9 demonstrated poor dispersibility. The paste obtained in Comparative Example 5 was, as described previously, not fluidic to be able to form no dispersion and unable to be evaluated by grind gage for dispersibility.

From the above results, it was demonstrated that pigments in the pigment dispersion paste of the present invention were uniformly dispersed in oil phase at high solid concentration in short period of time. Accordingly, the present invention can provide a pigment dispersion excellent in ease of dispersing pigments.

Example 12
(Preparation of Dispersion with Multiple Pigments-1)

According to the Table 1 below, the following components (a) through (d) were mixed well, then added to the mixture of components (e) and (f). The admixture was mixed and dispersed for 15 minutes at 8,000 rpm using a homogenizer (Tokushu Kika Kogyo Co., Ltd.) to obtain a pigment dispersion as an objective (oil dispersion slurry).

TABLE 1

Composition of Pigment Dispersion

| | Components | Amount (Parts by weight) |
|---|---|---|
| Surface treated pigments | a. product obtained from Example 1 | 5 |
| | b. product obtained from Example 2 | 2 |
| | c. product obtained from Example 3 | 1 |
| | d. product obtained from Example 4 | 0.2 |
| Oily materials | e. cyclomethicone (DC 345 Fluid, Dow Corning) | 60 |
| | f. Abil WE-09 (Goldschmidt) | 40 |

Example 13
(Preparation of Dispersion with Multiple Pigments-2)

According to the Table 2 below, the following components (a) through (d) were mixed well, then added to the mixture of components (e) and (f). The admixture was mixed and dispersed for 15 minutes at 8,000 rpm using a homogenizer (Tokushu Kika Kogyo Co., Ltd.) to obtain a pigment dispersion as an objective (oil dispersion slurry).

TABLE 2

Composition of Pigment Dispersion

| | Components | Amount (Parts by weight) |
|---|---|---|
| Surface treated pigments | a. product obtained from Example 5 | 5 |
| | b. product obtained from Example 2 | 2 |
| | c. product obtained from Example 6 | 1 |
| | d. product obtained from Example 4 | 0.2 |
| Oily materials | e. cyclomethicone (DC 345 Fluid, Dow Corning) | 60 |
| | f. Abil WE-09 (Goldschmidt) | 40 |

Comparative Example 10
(Preparation of Dispersion with Multiple Pigments-3)

According to the Table 3 below, the following components (a) through (d) were mixed well, then added to the mixture of components (e) and (f). The admixture was mixed and dispersed for 15 minutes at 8,000 rpm using a homogenizer (Tokushu Kika Kogyo Co., Ltd.) to obtain a pigment dispersion as an objective.

TABLE 3

Composition of Pigment Dispersion

| | Components | Amount (Parts by weight) |
|---|---|---|
| Surface treated pigments | a. product obtained from Comparative Example 1 | 5 |
| | b. product obtained from Comparative Example 2 | 2 |
| | c. product obtained from Comparative Example 3 | 1 |
| | d. product obtained from Comparative Example 4 | 0.2 |
| Oily materials | e. cyclomethicone (DC 345 Fluid, Dow Corning) | 60 |
| | f. Abil WE-09 (Goldschmidt) | 40 |

Example 14
(Evaluation of Dispersibility of Multiple Pigment Dispersion)

Dispersibility of multiple pigment dispersions (dispersions with multiple pigments) (oil dispersion slurry) obtained from Examples 12 and 13 and Comparative Example 10 was evaluated using a grind gage (Model 232, Ericsen).

(Evaluation Results)

Both multiple pigment dispersions obtained from Examples 12 and 13 demonstrated good dispersibility. Pigments in the multiple pigment dispersions of Examples 12 and 13 did not settle to the bottom even after standing for 15 minutes. In contrast, there were many undispersed pigments not smaller than 20 micro meter ($\mu$m) in the multiple pigment dispersion obtained from Comparative Example 10. In the multiple pigment dispersion of Comparative Example 10, there were also many pigments settled after standing for 15 minutes. Moreover, numerous undispersed pigments were confirmed when settled pigments were collected and streaked on a white paper with metal spatula.

From the above results, it was demonstrated that pigments in the multiple pigment dispersion of the present invention were uniformly dispersed in oil phase of the dispersion at a high solid concentration to the oily material in a short period of time, and also stable in the oily material. Accordingly, the multiple pigment dispersion of the present invention is excellent in ease of dispersing pigments. In contrast, pigments were not uniformly dispersed when multiple pigment dispersion (control) was produced in Comparative Example 10, and poor dispersion of pigments under standing was further degraded acceleratingly with time. Consequently, the present invention can provide a pigment dispersion, in which pigments are uniformly dispersed in the oily material (oil phase) at a high solid concentration and a stability to the oily material in a short period of time, excellent in ease of dispersing pigments.

Example 15

(Preparation of Cosmetic Product-1)

A liquid foundation was produced according to the composition of the following Table 4.

1. The following components of (a) through (d) were mixed well and pulverized by a sample mill (Hosokawa Micron). To the resulting mixture, components (e) and (f) were added and mixed until uniform.
2. Each of the following components (B) through (E) were heated individually to 60° C. to dissolve.
3. To the mixture obtained in (1) above (component (A)), added and mixed were the components (B) and (C), both were heated and dissolved in (2).
4. To the component (D) heated to dissolve in (2) was added and mixed the component (E) heated to dissolve in (2).
5. The water phase component mixture obtained from (4), which is a mixture of the components (D) and (E), was slowly added to the oil phase component mixture obtained from (3), which is a mixture of the components (A), (B) and (C), while mixing at 8,000 rpm using a homogenizer (Tokushu Kika Kogyo Co., Ltd.) to form an emulsion. After the emulsion was cooled, a desired cosmetic product, a liquid foundation, was obtained.

TABLE 4

Composition of Cosmetic Product (Liquid Foundation)

| | Components | Amount (Parts by weight) |
|---|---|---|
| (A) | a. mixture obtained from Example 1 | 9.0 |
| | b. mixture obtained from Example 2 | 3.2 |
| | c. mixture obtained from Example 3 | 0.7 |
| | d. mixture obtained from Example 4 | 0.2 |
| | e. cyclomethicone | 12.0 |
| | f. emulsified volatile oil | 2.0 |
| (B) | Propylparaben | 0.2 |
| | Polyoxyethylene lauryl ether | 0.5 |
| (C) | emulsified volatile oil | 18.0 |
| | Dimethicone (50 cs) | 3.0 |

TABLE 4-continued

Composition of Cosmetic Product (Liquid Foundation)

| | Components | Amount (Parts by weight) |
|---|---|---|
| | Tocopheryl acetate | 0.1 |
| | Corn oil | 0.05 |
| (D) | Methylparaben | 0.2 |
| | Propylene glycol | 8.0 |
| (E) | Pure water | To 100.0 |
| | Sodium dehydroacetate | 0.3 |
| | Pantothenyl alcohol | 0.2 |
| | Sodium chloride | 2.0 |

Example 16

(Preparation of Cosmetic Product-2)

A liquid foundation was produced according to the composition of the following Table 5.

1. The pigment dispersions from the following components of (a) through (d) were mixed well. To the resulting mixture, the following components (e) and (f) were added and mixed well.
2. Each of the following components (B) through (E) were heated individually to 60° C. to dissolve.
3. To the mixture obtained in (1) above (component (A)), added and mixed were the components (B) and (C), both were heated and dissolved in (2).
4. To the component (D) heated to dissolve in (2) was added and mixed the component (E) heated to dissolve in (2).
5. The water phase component mixture obtained from (4), which is a mixture of the components (D) and (E), was slowly added to the oil phase component mixture obtained from (3), which is a mixture of the components (A), (B) and (C), while mixing at 8,000 rpm using a homogenizer (Tokushu Kika Kogyo Co., Ltd.) to form an emulsion. After the emulsion was cooled, a desired cosmetic product, a liquid foundation, was obtained.

TABLE 5

Composition of Cosmetic Product (Liquid Foundation)

| | Components | Amount (Parts by weight) |
|---|---|---|
| (A) | a. dispersion obtained from Example 7 | 13.8 |
| | b. dispersion obtained from Example 8 | 4.9 |
| | c. dispersion obtained from Example 9 | 1.0 |
| | d. dispersion obtained from Example 10 | 0.3 |
| | e. cyclomethicone | 5.1 |
| | f. emulsified volatile oil | 2.0 |
| (B) | Propylparaben | 0.2 |
| | Polyoxyethylene lauryl ether | 0.5 |
| (C) | Emulsified volatile oil | 18.0 |
| | Dimethicone (50 cs) | 3.0 |
| | Tocopheryl acetate | 0.1 |
| | Corn oil | 0.05 |
| (D) | Methylparaben | 0.2 |
| | Propylene glycol | 8.0 |

TABLE 5-continued

Composition of Cosmetic Product (Liquid Foundation)

| | Components | Amount (Parts by weight) |
|---|---|---|
| (E) | Pure water | To 100.0 |
| | Sodium dehydroacetate | 0.3 |
| | Pantothenyl alcohol | 0.2 |
| | Sodium chloride | 2.0 |

The pigment dispersion, (oil dispersion) of the present invention provided a cosmetic product, a liquid foundation, with stable quality in color (refer to Example 17 after) and viscosity and the like with a simpler process in which a pulverizing process by an atomizer or the like is unnecessary.

Comparative Example 11

(Preparation of Cosmetic Product-3)

A liquid foundation was produced according to the composition of the following Table 6.

1. The following components of (a) through (d) were mixed well and pulverized by a sample mill (Hosokawa Micron). To the resulting mixture, the following components (e) and (f) were added and mixed until uniform.
2. Each of the following components (B) through (E) were heated individually to 60° C. to dissolve.
3. To the mixture obtained in (1) above (component (A)), added and mixed were the components (B) and (C), both were heated and dissolved in (2).
4. To the component (D) heated to dissolve in (2) was added and mixed the component (E) heated to dissolve in (2).
5. The water phase component mixture obtained from (4), which is a mixture of the components (D) and (E), was slowly added to the oil phase component mixture obtained from (3), which is a mixture of the components (A), (B) and (C), while mixing at 8,000 rpm using a homogenizer (Tokushu Kika Kogyo Co., Ltd.) to form an emulsion. After the emulsion was cooled, a desired cosmetic product, a liquid foundation, was obtained.

TABLE 6

Composition of Cosmetic Product (Liquid Foundation)

| | Components | Amount (Parts by weight) |
|---|---|---|
| (A) | a. mixture obtained from Example 1 | 9.0 |
| | b. mixture obtained from Example 2 | 3.2 |
| | c. mixture obtained from Example 3 | 0.7 |
| | d. mixture obtained from Example 4 | 0.2 |
| | e. cyclomethicone | 12.0 |
| | f. emulsified volatile oil | 2.0 |
| (B) | Propylparaben | 0.2 |
| | Polyoxyethylene lauryl ether | 0.5 |
| (C) | emulsified volatile oil | 18.0 |
| | Dimethicone (50 cs) | 3.0 |
| | Tocopheryl acetate | 0.1 |
| | Corn oil | 0.05 |

TABLE 6-continued

Composition of Cosmetic Product (Liquid Foundation)

| | Components | Amount (Parts by weight) |
|---|---|---|
| (D) | Methylparaben | 0.2 |
| | Propylene glycol | 8.0 |
| (E) | Pure water | To 100.0 |
| | Sodium dehydroacetate | 0.3 |
| | Pantothenyl alcohol | 0.2 |
| | Sodium chloride | 2.0 |

Example 17

(Evaluation of Cosmetic Products; Examination for Dispersibility of Pigments)

The cosmetic products (liquid foundations) obtained from the Examples 15 and 16, and the Comparative Example 11 were evaluated based on a pigment dispersion quality (dispersibility).

Two drops of liquid foundation obtained from the Example 15 were placed on a slide glass and covered by another slide glass. The slide glasses were moved right and left while pressed by fingers to examine presence of undispersed pigments. The liquid foundations obtained from the Example 16 and the Comparative Example 11 were examined in the same manner.

As a result of the examination, uniform dispersion of pigments and absence of undispersed pigments in the liquid foundations of the Examples 15 and 16 were confirmed. In contrast, presence of undispersed pigments was confirmed by observation of red streak in the liquid foundation of the Comparative Example 11.

These were further examined under video microscope (Olympus) with magnification of 200. Pigments were uniformly dispersed and undispersed pigments were not observed in the liquid foundations of the Examples 15 and 16. In contrast, presence of white specks (titanium dioxide), red specks (red iron oxide), and undispersed pigments was confirmed in the liquid foundation of the Comparative Example 11.

As described above, it is obvious that in the cosmetic products of the present invention, pigments are uniformly dispersed with high stability, in short period of time, at a high concentration in oil phase of the cosmetic products. Such cosmetic products may be prepared easily. Therefore, cosmetic products with excellent emulsion stability, superior application felling (smooth feeling) compared to the existing cosmetic products can be provided according to the present invention.

Effect of Invention

The present invention provides a surface treated pigment which can be easily and uniformly dispersed in a short period of time in a cosmetically acceptable oily material. The present invention can also provide a pigment dispersion, containing high level (concentration) of said surface treated pigment, with excellent dispersion stability and versatility (ease of dispersion and wide rage of usage).

Further, using said pigment dispersion, a cosmetic product with excellent emulsion stability and superior application feeling and the like can be prepared with a simple process. Therefore, the present invention is especially useful in a cosmetic industry.

What is claimed is:

1. A pigment for a cosmetic product, wherein particles contained in the pigment are surface treated with at least one of N-acylglycine hydroxyaluminum and N-acyl-N-methylglycine hydroxyaluminum.

2. The pigment as defined in claim 1, wherein the N-acyl groups of said N-acylglycine hydroxyaluminum and said N-acyl-N-methylglycine hydroxyaluminum are selected from the group consisting of a N-myristoyl group, a N-lauroyl group, a N-palmitoyl group, or a N-stearoyl group.

3. The pigment as defined in claim 1, wherein the N-acyl groups of said N-acylglycine hydroxyaluminum and said N-acyl-N-methylglycine hydroxyaluminum are N-myristoyl groups.

4. The pigment as defined in any one of claims 1 to 3, wherein the particles to be treated are selected from the group consisting of titanium oxides and iron oxides.

5. A pigment dispersion comprising the surface treated particles as defined in any one of claims 1 to 3 and a cosmetically acceptable oily material.

6. The pigment dispersion as defined in claim 5, which has fluidity.

7. The pigment dispersion as defined in claim 5, wherein the viscosity is equal to or less than 100,000 mPa.sec.

8. The pigment dispersion as defined in claim 5, wherein said cosmetically acceptable oily material is at least one material selected from the group consisting of silicone oils and fatty acid ester oils.

9. The pigment dispersion as defined in claim 5, which contains from 40 to 70 wt % of said surface treated particles, and from 30 to 60 wt % of said cosmetically acceptable oily material.

10. A cosmetic product comprising the surface treated particles as defined in any one of claims 1 to 3.

11. The cosmetic product as defined in claim 10, which contains from 1 to 50 wt % of said surface treated particles.

12. The cosmetic product as defined in claim 10, which contains from 5 to 99 wt % of said cosmetically acceptable oily material and from 0 to 94 wt % water.

13. A cosmetic product comprising the pigment dispersion as defined in claim 5.

14. The cosmetic product as defined in claim 13, which contains from 1.5 to 50 wt % of said pigment dispersion.

15. The cosmetic product as defined in claim 13, which contains from 0 to 94 wt % water.

16. The cosmetic product as defined in claim 10, which is a liquid foundation, a lip gloss, an eyeliner, a mascara, a cream eye-shadow, a tinted moisturizer, or a sunscreen product.

17. The cosmetic product as defined in claim 13, which is a liquid foundation, a lip gloss, an eyeliner, a mascara, a cream eye-shadow, a tinted moisturizer, or a sunscreen product.

* * * * *

UNITED STATES PATENT AND TRADEMARK OFFICE
CERTIFICATE OF CORRECTION

| | | |
|---|---|---|
| PATENT NO. | : 6,790,452 B2 | Page 1 of 1 |
| APPLICATION NO. | : 10/178890 | |
| DATED | : September 14, 2004 | |
| INVENTOR(S) | : Shigeru Kishida et al. | |

It is certified that error appears in the above-identified patent and that said Letters Patent is hereby corrected as shown below:

<u>In Column 15, Line 53 should read:</u>

(A)    a. mixture obtained from --Comparative--    9.0

<u>In Column 15, Line 55 should read:</u> b. mixture obtained from --Comparative--    3.2

<u>In Column 15, Line 57 should read:</u> c. mixture obtained from --Comparative--    0.7

<u>In Column 15, Line 59 should read:</u> d. mixture obtained from --Comparative--    0.2

Signed and Sealed this

Twenty-fifth Day of November, 2008

JON W. DUDAS
*Director of the United States Patent and Trademark Office*